(12) United States Patent
Weiss et al.

(10) Patent No.: US 12,196,625 B2
(45) Date of Patent: Jan. 14, 2025

(54) SYSTEM AND METHOD FOR MONITORING A CHANGE OVER TIME OF A PHYSICAL MEDIUM USING ULTRASONIC WAVE SENSING ELEMENTS EMBEDDED THEREIN

(71) Applicant: GREENVIBE WN SENSING TECHNOLOGIES LTD., Beer Sheva (IL)

(72) Inventors: Oran Weiss, Haifa (IL); Oleg Naigertsik, Haifa (IL)

(73) Assignee: GREENVIBE WN SENSING TECHNOLOGIES LTD., Beer Sheva (IL)

( * ) Notice: Subject to any disclaimer, the term of this patent is extended or adjusted under 35 U.S.C. 154(b) by 738 days.

(21) Appl. No.: 17/151,171

(22) Filed: Jan. 17, 2021

(65) Prior Publication Data

US 2021/0140924 A1 May 13, 2021

Related U.S. Application Data

(63) Continuation-in-part of application No. 16/769,915, filed as application No. PCT/IL2018/051329 on Dec. 4, 2018, now Pat. No. 11,933,680.

(30) Foreign Application Priority Data

Dec. 4, 2017 (IL) .......................... 256108

(51) Int. Cl.
*G01L 1/12* (2006.01)
*A61M 5/50* (2006.01)
(Continued)

(52) U.S. Cl.
CPC .............. *G01L 1/125* (2013.01); *G01L 1/241* (2013.01); *G01N 3/08* (2013.01); *G01N 29/043* (2013.01);
(Continued)

(58) Field of Classification Search
CPC ........... G01L 1/125; G01L 1/241; G01N 3/08; G01N 29/043; G01N 29/07; G01N 29/223;
(Continued)

(56) References Cited

U.S. PATENT DOCUMENTS 4,763,927 A 8/1988 Schneider
4,766,516 A 8/1988 Ozdemir et al.
(Continued)

FOREIGN PATENT DOCUMENTS

CN 2401940 10/2000
CN 101735614 6/2010
(Continued)

OTHER PUBLICATIONS

IN-201641024214 OCR text; Shah et al.; Published Jan. 19, 2018. (Year: 2018); Filed Jul. 15, 2016.*
(Continued)

*Primary Examiner* — Daniel Pihulic
(74) *Attorney, Agent, or Firm* — PEARL COHEN ZEDEK LATZER BARATZ LLP

(57) ABSTRACT

A system and a method of monitoring physical properties of a physical medium over time are provided herein. The method may include the following steps: embedding a plurality of acoustic sensors into a physical medium before curing thereof; transmitting an acoustic wave by at least one transmitter coupled to or embedded within said physical medium; repeatedly calculating, over different points of time, a travel time of said acoustic wave between the at least one transmitter and the plurality of acoustic sensors; and analyzing said travel times, to detect a change over time in physical properties of said physical medium associated with said travel time.

18 Claims, 13 Drawing Sheets

(51) Int. Cl.

| | |
|---|---|
| *G01L 1/24* | (2006.01) |
| *G01N 3/08* | (2006.01) |
| *G01N 29/04* | (2006.01) |
| *G01N 29/07* | (2006.01) |
| *G01N 29/22* | (2006.01) |
| *G01N 29/44* | (2006.01) |
| *G01N 33/38* | (2006.01) |
| *G06K 19/073* | (2006.01) |
| *G07D 7/2033* | (2016.01) |
| *H04B 11/00* | (2006.01) |
| *H10N 30/30* | (2023.01) |
| *H10N 30/857* | (2023.01) |

(52) U.S. Cl.
CPC .......... *G01N 29/07* (2013.01); *G01N 29/223* (2013.01); *G01N 33/383* (2013.01); *H04B 11/00* (2013.01); *H10N 30/302* (2023.02); *H10N 30/857* (2023.02); *A61M 5/5086* (2013.01); *G01N 29/04* (2013.01); *G01N 29/4409* (2013.01); *G01N 2203/0092* (2013.01); *G01N 2291/025* (2013.01); *G01N 2291/0251* (2013.01); *G06K 19/07372* (2013.01); *G07D 7/2033* (2013.01)

(58) Field of Classification Search
CPC ................. G01N 33/383; G01N 29/04; G01N 29/4409; G01N 2203/0092; G01N 2291/025; G01N 2291/0251; H04B 11/00; H10N 30/302; H10N 30/857; A61M 5/5086; G06K 19/07372; G07D 7/2033
See application file for complete search history.

(56) References Cited

U.S. PATENT DOCUMENTS

| | | | |
|---|---|---|---|
| 4,792,667 A | 12/1988 | Chen | |
| 6,370,964 B1 | 4/2002 | Chang et al. | |
| 6,848,049 B1 | 1/2005 | Tailliet | |
| 8,516,269 B1 | 8/2013 | Hamlet et al. | |
| 9,230,050 B1 | 1/2016 | Lanzerotti | |
| 9,515,157 B2 | 12/2016 | Woerdenweber | |
| 2003/0054158 A1 | 3/2003 | Smith et al. | |
| 2003/0194578 A1 | 10/2003 | Tam et al. | |
| 2003/0204743 A1 | 10/2003 | Devadas et al. | |
| 2008/0002882 A1 | 1/2008 | Voloshynovskyy et al. | |
| 2008/0169833 A1 | 7/2008 | Anderson et al. | |
| 2008/0282209 A1 | 11/2008 | Anderson et al. | |
| 2008/0303376 A1 | 12/2008 | Jakli et al. | |
| 2009/0100392 A1 | 4/2009 | Ivaldi | |
| 2009/0306920 A1 | 12/2009 | Zwinger et al. | |
| 2010/0213951 A1 | 8/2010 | Lewis | |
| 2010/0237854 A1 | 9/2010 | Kumhyr et al. | |
| 2010/0241864 A1 | 9/2010 | Kelley et al. | |
| 2011/0148457 A1 | 6/2011 | Abramovici | |
| 2011/0264921 A1 | 10/2011 | Keil | |
| 2012/0051389 A1 | 3/2012 | Schalles et al. | |
| 2012/0179812 A1 | 7/2012 | Keller, III | |
| 2012/0212253 A1 | 8/2012 | Lewis | |
| 2012/0223403 A1 | 9/2012 | Keller, III et al. | |
| 2012/0317662 A1 | 12/2012 | Neo et al. | |
| 2013/0127442 A1 | 5/2013 | Satoh et al. | |
| 2013/0141137 A1 | 6/2013 | Krutzik et al. | |
| 2013/0147511 A1 | 6/2013 | Koeberl et al. | |
| 2013/0222109 A1 | 8/2013 | Lim | |
| 2013/0276059 A1 | 10/2013 | Lewis et al. | |
| 2013/0318607 A1 | 11/2013 | Reed et al. | |
| 2014/0100807 A1 | 4/2014 | Rosenblatt et al. | |
| 2014/0103344 A1 | 4/2014 | Tehranipoor et al. | |
| 2014/0252487 A1 | 9/2014 | Stephens et al. | |
| 2014/0253222 A1 | 9/2014 | Merchant et al. | |
| 2014/0258156 A1 | 9/2014 | Tziazas et al. | |
| 2014/0271365 A1 | 9/2014 | Pathak et al. | |
| 2015/0078518 A1 | 3/2015 | Tziazas et al. | |
| 2015/0130506 A1 | 5/2015 | Bhunia et al. | |
| 2015/0137830 A1 | 5/2015 | Keller, III et al. | |
| 2015/0207627 A1 | 7/2015 | Yamamoto et al. | |
| 2015/0219714 A1 | 8/2015 | Hamilton et al. | |
| 2015/0247892 A1 | 9/2015 | Robertazzi et al. | |
| 2015/0260786 A1 | 9/2015 | Hampel et al. | |
| 2015/0269592 A1 | 9/2015 | Hieftje et al. | |
| 2015/0301109 A1 | 10/2015 | O'Flynn | |
| 2015/0358337 A1 | 12/2015 | Keller | |
| 2016/0047855 A1 | 2/2016 | Bhunia et al. | |
| 2016/0047932 A1 | 2/2016 | Akaba et al. | |
| 2016/0072632 A1 | 3/2016 | Blanton | |
| 2016/0080153 A1 | 3/2016 | Suzuki | |
| 2016/0103065 A1 | 4/2016 | Lee et al. | |
| 2016/0124041 A1 | 5/2016 | Pathak et al. | |
| 2021/0131883 A1* | 5/2021 | Naigertsik | G01L 1/241 |
| 2021/0140924 A1* | 5/2021 | Weiss | G01N 3/08 |

FOREIGN PATENT DOCUMENTS

| | | | |
|---|---|---|---|
| CN | 101909408 | 12/2010 | |
| CN | 101944194 | 1/2011 | |
| CN | 102147875 | 8/2011 | |
| CN | 201993789 U | 9/2011 | |
| CN | 102306318 | 1/2012 | |
| CN | 102436619 | 5/2012 | |
| CN | 102467677 | 5/2012 | |
| CN | 104101792 | 10/2014 | |
| CN | 104321874 | 1/2015 | |
| CN | 105218087 | 1/2016 | |
| CN | 104457964 | 7/2017 | |
| CN | 108196188 | 6/2018 | |
| EP | 1020813 | 7/2000 | |
| EP | 1674862 | 6/2006 | |
| EP | 2950233 | 12/2015 | |
| EP | 3721205 | 8/2021 | |
| EP | 3721205 A4 * | 8/2021 | G01L 1/125 |
| GB | 2460071 | 11/2009 | |
| IL | 133460 | 10/2003 | |
| IL | 256108 | 6/2019 | |
| IL | 256108 A * | 6/2019 | G01L 1/125 |
| IN | 201641024214 | 1/2018 | |
| JP | 2000-276627 | 10/2000 | |
| JP | 2019 197046 | 11/2019 | |
| WO | WO 0017826 | 3/2000 | |
| WO | WO 2010/105993 | 9/2010 | |
| WO | WO 2014/075617 | 5/2014 | |
| WO | WO 2015/081163 | 6/2015 | |
| WO | WO 2015/089346 | 6/2015 | |
| WO | WO 2015/140731 | 9/2015 | |
| WO | WO 2019/111252 | 6/2019 | |
| WO | WO-2019111252 A1 * | 6/2019 | G01L 1/125 |
| WO | WO 2022/153317 | 7/2022 | |
| WO | WO-2022153317 A1 * | 7/2022 | |

OTHER PUBLICATIONS

Chenglu Jin et al., "Secure and Efficient Initialization and Authentication Protocols for SHIELD"; University of Connecticut, Jun. 27, 2015, pp. 1-24.

Steve H. Weingart, "Physical Security Devices for Computer Subsystems: A Survey of Attacks and Defenses", Secure Systems and Smart Card Group IBM, Thomas J. Watson Research Center, Hawthorne, NY; CHES 2000, LNCS 1965, pp. 302-317, 2000.

Broad Agency Announcement, Supply Chain Hardware Integrity for Electronics Defense (SHIELD), Microsystems Technology Office, DARPA-BAA-14-16, Mar. 3, 2014, pp. 3-54.

Defense Advanced Research Projects Agency, Microsystems Technology Office, Special Notice, SHIELD Proposers' Day, DARPA-SN-14-22, Feb. 2014.

Statement by Arati Prabhakar, Director, Defense Advanced Research Projects Agency (DARPA) Before the Subcommittee on Emerging Threats and Capabilities, Armed Services Committee, U.S. House of Representatives; Department of Defense Fiscal Year 2017 Science and Technology Programs: Defense Innovation to Create the Future Military Force, Feb. 24, 2016, pp. 1-23.

(56) References Cited

OTHER PUBLICATIONS

Davood Shahrjerdi et al., "Shielding and Securing Integrated Circuits with Sensors"; 2014 IEEE; pp. 170-174.
Joe Grand, "Practical Secure Hardware Design for Embedded Systems", Grand Idea Studio, Inc., this paper was originally published by CMP Media in the Proceedings of the 2004 Embedded Systems Conference, San Francisco, California, Mar. 29-Apr. 1, 2004; Last updated on Jun. 23, 2004.
"Winning the Battle Against Counterfeit Semiconductor Products", A report of the SIA Anti-Counterfeiting Task Force, Aug. 2013, pp. 1-27.
International Search Report for PCT Application No. PCT/IL2018/051329, mailed on Mar. 5, 2019.
Office Action for Israel Patent Application No. 133460, mailed on Oct. 30, 2019.
Huang Wenbin et al; Cracks monitoring and characterization using BaSrTiOflexoelectric strain gradient sensors; Proceedings Of Spie; IEEE, US, vol. 9061; Mar. 8, 2014.
Shun-Di Hu et al; Signal analysis of flexoelectric transducers on rings; Piezoelectricity, Acoustic Waves and Device Applications; SPAWDA; 2010 Symposium On, IEEE; Dec. 10, 2010.
Rey Alejandro D. et al; Stress Sensor Device Based on Flexoelectric Liquid Crystalline Membranes; CHEMPHYSCHEM—A European Journal of Chemical Physics and Physical Chemistry; vol. 15, No. 7; Oct. 2, 2013.
Mark Hodnett et al; High-frequency acoustic emissions generated by a 20 KHz sonochemical horn processor detected using a novel broadband acoustic sensor: a preliminary study; Ultrasonics Sonochemistry 11 (2004) 441-454; Sep. 1, 2004.
Harsh Shah et al; In-situ process- and online structural health-monitoring of composites using embedded acoustic waveguide sensors; Journal of Physics Communication; Dec. 7, 2017.

* cited by examiner

210 — embedding a plurality of acoustic sensors into a physical medium before curing thereof; transmitting an acoustic wave by at least one transmitter coupled to or embedded within said physical medium 220 — repeatedly calculating, over different points of time, a travel time of said acoustic wave between the at least one transmitter and the plurality of acoustic sensors 240 — analyzing said travel times, to detect a change over time in physical properties of said physical medium associated with said travel time

| Piezo vs. medium status LUT |||
|---|---|---|
| reading | Piezo readings (volt) | Medium status |
| 1 | 0.25 | Newly cured |
| 2 | 0.33 | Young |
| 3 | 0.45 | Old |
| 4 | 0.80 | Dangerous |

700A

700B

SYSTEM AND METHOD FOR MONITORING A CHANGE OVER TIME OF A PHYSICAL MEDIUM USING ULTRASONIC WAVE SENSING ELEMENTS EMBEDDED THEREIN

CROSS REFERENCE TO RELATED APPLICATIONS

This application is a continuation-in-part of U.S. patent application Ser. No. 16/769,915, filed on Jun. 4, 2020, which is a US national state application of PCT International Patent Application No. PCT/IL2018/051329, filed on Dec. 4, 2018, which claims the benefit of Israeli Patent Application No. 256108, filed on Dec. 4, 2017, all of which are incorporated herein by reference in their entireties.

FIELD OF THE INVENTION

The present invention relates generally to the field of sensing changes of physical properties within materials over time using sensors.

BACKGROUND OF THE INVENTION

Many construction and other materials (hereinafter referred to as "physical medium") tend to undergo changes affecting their physical properties over time. Some of these changes are crucial for determining the quality of the material and their endurance.

Some of these materials are prepared from one or more liquid or other substances and undergo a solidifying or curing process during which the reach, after a transient period, their final strength. It is important to make sure that the curing process was performed correctly as this also affects the strength of the cured material.

Traditional methods of survey include manual periodical checks of these materials. One known method involves sending an acoustic wave into the material from outside the material and analyzing the reflection arriving from the material.

All current monitoring methods necessitate a visit of a technician where the testing equipment is not always calibrated and vary from one visit to another. In addition, the current monitoring methods cannot test the quality of the material in a plurality of locations at the same time.

It is also difficult to assess the implication of the curing process on the aging process of the material, since data relevant to the transient period in which the material solidified are unknown.

It would, therefore, be advantageous to provide a method and a system for on-site monitoring the aging process of these material possibly taking into account the data relevant to the curing process thereof.

The discussion above is presented as a general overview of related art in this field and should not be construed as an admission that any of the information it contains constitutes prior art against embodiments of present patent application discussed hereinafter.

BRIEF SUMMARY OF THE INVENTION

Some embodiments of the present invention provide system and a method of monitoring physical properties of a media over time are provided herein. The method may include the following steps: embedding a plurality of acoustic sensors into a physical medium before curing thereof; transmitting an acoustic wave by at least one transmitter coupled to or embedded within said physical medium; repeatedly calculating, over different points of time, a travel time of said acoustic wave between the at least one transmitter and the plurality of acoustic sensors; and analyzing said travel times, to detect a change over time in physical properties of said physical medium associated with said travel time.

Some embodiments may include a plurality of sensors, connected together within an article of manufacture, with a main sensor from which a power socket will lead out externally for connection to a power supply for charging all the sensors.

Some embodiments may further include a power transition line connected the main sensor of the plurality of sensors to the structural power supply.

Some embodiments may further include sensors located close enough to a wireless recharge device to enable energy transfer through radio frequency electromagnetic waves.

Some embodiments may further include a power distribution unit comprising a battery which may be able to be charged using radio frequency electromagnetic waves.

According to some embodiments of the present invention, the apparatus may include a main sensor module which may comprise a central processing unit and a data transmission module; further sensing modules may comprise a temperature meter and simple circuit, and furthermore the data may be transmitted through a wired connection to the main sensor module or via a wireless communication protocol to the main hub.

Some embodiments may further include one or more secondary hubs that receive data from sensors and transmit and to the main hub, wherein the main hub transmits the data to the internet, wherein the data transfer is achieved via at least one of: 3G/4G/5G communication, autonomous vehicle linkage and satellite communication.

Some other embodiments provide a system for detecting usage condition of an article of manufacture. The system may include: a ferro-elastic substance, physically coupled to said article of manufacture and configured to undergo a change in at least one physical property thereof, responsive to a change in said at least one of: the manufacturing process and the usage condition of said article of manufacture, wherein said change in the at least one physical property is irreversible, and wherein said change in usage condition comprises at least a first usage of said article of manufacture post manufacturing thereof; and at least one detector configured to sense said change in the at least one physical property of said substance.

According to some embodiments of the present invention, the physical medium may consist of glue or concrete, and may further comprise a ferro-elastic portion. Over the duration of the transient period, the compound may be subject to numerous stresses and strains due to changing external, environmental conditions.

The ferro elastic portion of the compound may take on these forces and may further retain the history of said forces that it underwent over the transient period. In examining the forces that the ferro-elastic portion underwent, a more general picture and awareness of the changes that the compound goes through may be ascertained.

Namely, in analyzing the change in polarization of the ferro-elastic material, a property whose changes are indicative of the overall effects on the compound may be ascertained. The polarization changes may be detected via sensors, and a look-up table may be consulted to determine the exact nature of the detected changes and thus the larger implications for the compound in which the ferro-elastic material resided during the transient period.

According to some embodiments of the present invention, the system may further include an in-situ presence indicator for detecting the presence of pedestrians or vehicles in the vicinity of the detector, configured to take account of excess strain Some other embodiments of the invention may provide a system including a door traffic counter in a predefined place within the vicinity of the detector, configured to take account of excess strain.

Some other embodiments provide a method for detecting at least one of: a usage condition and a manufacturing process of an article of manufacture, the method may include: physically coupling a substance, to said article of manufacture and configured to undergo a change in at least one physical property thereof, responsive to a change in said at least one of: the manufacturing process and the usage condition of said article of manufacture; and sensing said change in the at least one physical property of said substance, wherein said change in the at least one physical property is irreversible, and wherein said change in usage condition comprises at least a first usage of said article of manufacture post manufacturing thereof.

According to some embodiments of the present invention, an array of sensors may be distributed in predefined places to provide relevant information regarding the structure, known as Structure Health Monitoring (SHM). The sensors may be calibrated to provide more accurate readings of ferro-elastic behavior; if offset occurs, this may be cancelled out by software manipulation.

According to some embodiments of the present invention, the step of physically coupling is carried out at a specific point of time based on physical properties of at least one of: the usage condition and the manufacturing process of an article of manufacture.

These additional, and/or other aspects and/or advantages of the present invention are set forth in the detailed description which follows.

BRIEF DESCRIPTION OF THE DRAWINGS

For a better understanding of the invention and in order to show how it may be implemented, references are made, purely by way of example, to the accompanying drawings in which like numerals designate corresponding substances or sections. In the accompanying drawings:

FIG. 2 shows a flowchart diagram of a method using acoustic sensors embedded in a physical medium for monitoring the physical condition of the physical medium over time, according to some embodiments of the present invention;

Figure 1A:
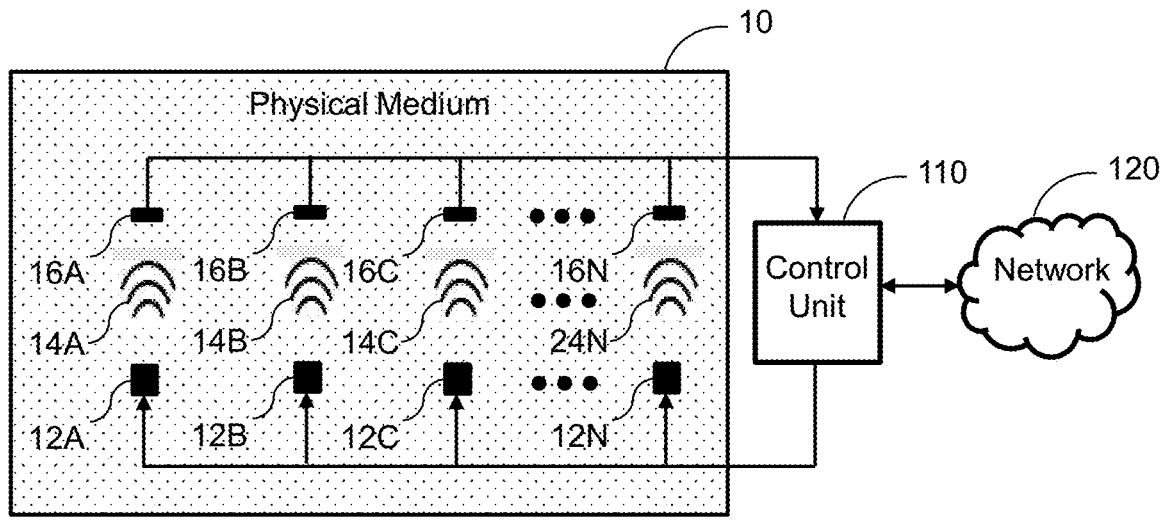
FIGS. 1A and 1B are block diagrams illustrating a system for monitoring physical medium via acoustic sensors embedded therein, according to some embodiments of the present invention.

It will be appreciated that, for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

Prior to the description of the invention being set forth, it may be helpful to provide definitions of certain terms that will be used hereinafter.

The term "Ultrasonic Pulse Velocity" (UPV) as used herein is defined as an in-situ, nondestructive test to check the quality of a material such as concrete and natural rocks. In this test, the strength and quality of concrete or rock is assessed by measuring the velocity of an ultrasonic pulse passing through a concrete structure or natural rock formation.

This test is conducted by passing a pulse of ultrasonic wave through concrete to be tested and measuring the time taken by pulse to get through the structure. Higher velocities indicate good quality and continuity of the material, while slower velocities may indicate concrete with many cracks or voids.

Ultrasonic testing equipment includes a pulse generation circuit, consisting of electronic circuit for generating pulses and a transducer (e.g. emitter) for transforming electronic pulse into mechanical pulse (e.g. acoustic wave) having an oscillation frequency in range of tens of kHz, and a pulse reception circuit (e.g. receiver) that receives the signal.

The term "sensing element" as used herein is defined as the aforementioned transducer for transforming electronic pulse into mechanical pulse and a pulse reception circuit that receives the signal paired within a predefined distance between them. The sensing element is suitable for embedding or coupling into the material (e.g. concrete) during or before curing thereof.

The term "signal generator" as used herein is defined as an oscillator configured to apply an oscillation frequency in range of 40 kHz to 50 kHz to a transducer for transforming electronic pulse into mechanical pulse.

The term "central processing unit" or "processor" as used herein is a hardware- and software-based device used for processing the data retrieved from the sensing element.

The term "physical medium", "physical media", "substance", or "material" as used herein is defined as any material in which at least one sensing element is embedded or coupled thereto before or during the curing thereof.

The term "ferro-elastic" as used herein is defined as a material able to exhibit a spontaneous strain. When stress is applied to a ferro-elastic material, a phase change will occur in the material from one phase to an equally stable phase, either of different crystal structure (e.g. cubic to tetragonal), or of different orientation (a 'twin' phase). This stress-induced phase change results in a strain gradient in the material. The pressure applied to the ferro-elastic material may generate a pressure-induced polarization or partial polarization, which exists as long as the strain gradient is maintained. In accordance with an alternative definition, "flexoelectricity" being the property of "ferro-elastic" material is the response of the dielectric polarization to a macroscopic strain gradient.

With specific reference now to the drawings in detail, it is stressed that the particulars shown are for the purpose of example and solely for discussing the preferred embodiments of the present invention and are presented in the cause of providing what is believed to be the most useful and readily understood description of the principles and conceptual aspects of the invention. In this regard, no attempt is made to show structural details of the invention in more detail than is necessary for a fundamental understanding of the invention. The description taken with the drawings makes apparent to those skilled in the art how the several forms of the invention may be embodied in practice.

Before the embodiments of the invention are explained in detail, it is to be understood that the invention is not limited in its application to the details of construction and the arrangement of the components set forth in the following descriptions or illustrated in the drawings. The invention is applicable to other embodiments and may be practiced or carried out in various ways. Also, it is to be understood that the phraseology and terminology employed herein is for the purpose of description and should not be regarded as limiting.

Figure 1B:
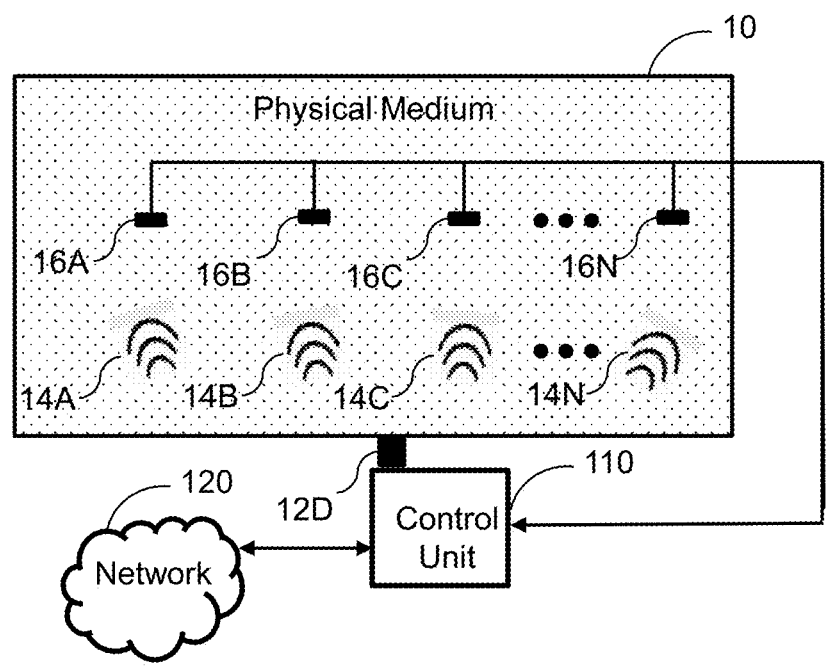

FIGS. 1A and 1B are block diagrams illustrating a system for monitoring physical medium 10 via acoustic sensors 16A-16N embedded therein, according to some embodiments of the present invention. A system 100A of monitoring a change in physical properties of a media over time, the system includes: a plurality of acoustic sensors 16A-16N embedded within a physical medium before curing thereof; a transmitter 12-A-12N coupled to or embedded within said physical medium which transmits one or more acoustic waves 14A-14N; and at least one computer processor on a control unit 110 which repeatedly calculates, over different points of time, a travel time of said acoustic wave between the at least one transmitter and the plurality of acoustic sensors, wherein said computer processor analyzes said travel times, to detect a change over time in physical properties of said physical medium associated with said travel time.

FIG. 2 shows a flowchart diagram of a method using acoustic sensors embedded in a physical medium for monitoring the physical condition of the physical medium over time, according to some embodiments of the present invention. A method 200 of monitoring a change in physical properties of a media over time comprises: embedding a plurality of acoustic sensors into a physical medium before curing thereof 210; transmitting an acoustic wave by at least one transmitter coupled to or embedded within said physical medium 220; repeatedly calculating, over different points of time, a travel time of said acoustic wave between the at least one transmitter and the plurality of acoustic sensors 230; and analyzing said travel times, to detect a change over time in physical properties of said physical medium associated with said travel time 240.

Figure 3:
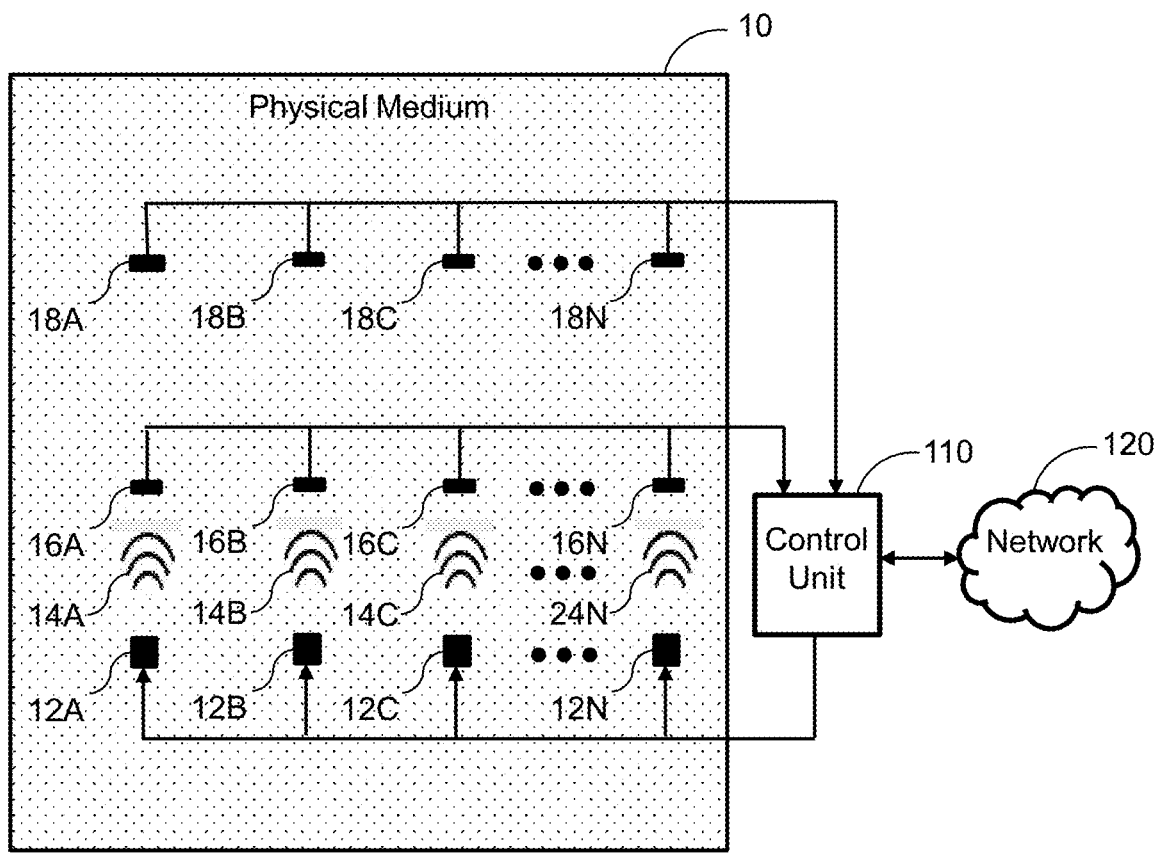
FIG. 3 is block diagram illustrating a system for monitoring physical medium using a combination of acoustic sensors and ferro-elastic sensors embedded therein, according to some embodiments of the present invention.

FIG. 3 is block diagram illustrating a system for monitoring physical medium using a combination of acoustic sensors and ferro-elastic sensors embedded therein, according to some embodiments of the present invention; A system of monitoring a change in physical properties of a media over time comprises: a plurality of acoustic sensors embedded within a physical medium before curing thereof; a transmitter coupled to or embedded within said physical medium which transmits one or more acoustic waves; and at least one computer processor which repeatedly calculates, over different points of time, a travel time of said acoustic wave between the at least one transmitter and the plurality of acoustic sensors, wherein said computer processor analyzes said travel times, to detect a change over time in physical properties of said physical medium associated with said travel time.

Figure 4:
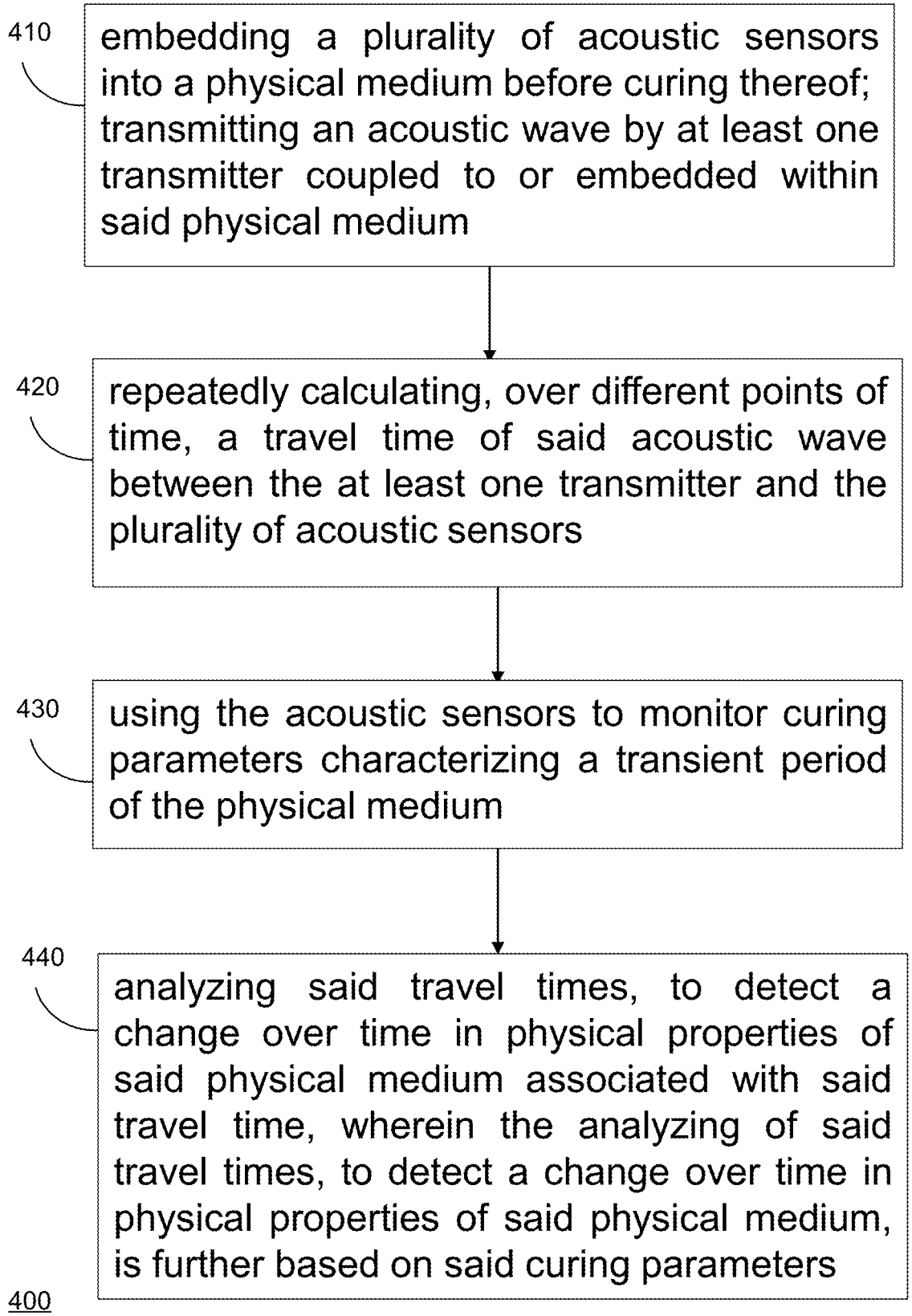
FIG. 4 shows a flowchart diagram of a method using a combination of acoustic sensors and ferro-elastic sensors embedded in a physical medium for monitoring the physical condition of the physical medium over time, according to some embodiments of the present invention.

FIG. 4 shows a flowchart diagram of a method using a combination of acoustic sensors and ferro-elastic sensors embedded in a physical medium for monitoring the physical condition of the physical medium over time, according to some embodiments of the present invention. A method of monitoring a change in physical properties of a media over time, method 400 comprising: embedding a plurality of acoustic sensors into a physical medium before curing thereof 410; transmitting an acoustic wave by at least one transmitter coupled to or embedded within said physical medium 420; repeatedly calculating, over different points of time, a travel time of said acoustic wave between the at least one transmitter and the plurality of acoustic sensors 430; using the acoustic sensors to monitor curing parameters characterizing a transient period of the physical medium 440; and analyzing of said travel times, to detect a change over time in physical properties of said physical medium, further based on said curing parameters.

Figure 5:
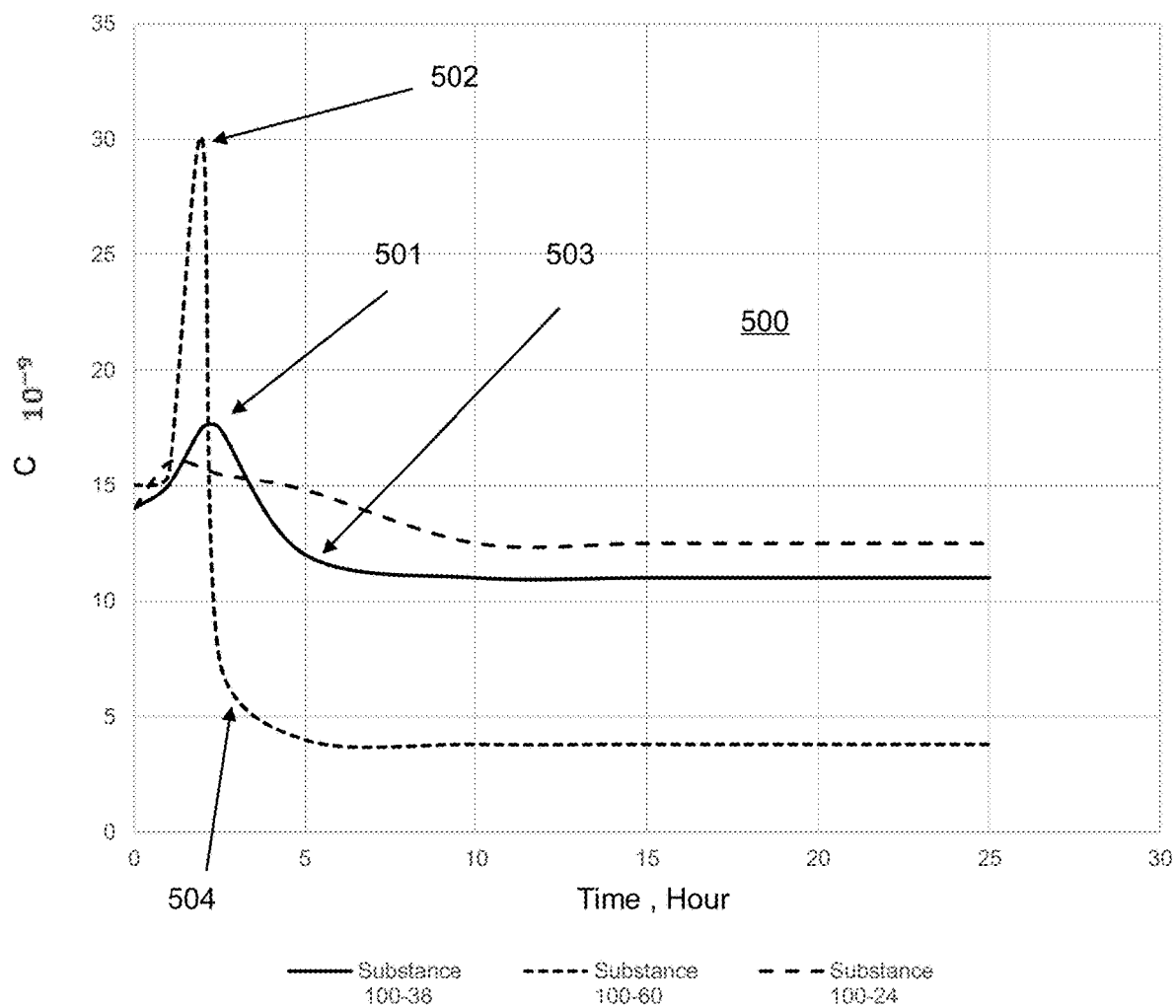
FIG. 5 shows a graph diagram illustrating a change in property of a physical medium over time, exhibiting a transient period associated with curing thereof, according to some embodiments of the present invention.

FIG. 5 shows a graph diagram illustrating a change in property of a physical medium over time, exhibiting a transient period associated with curing thereof, according to some embodiments of the present invention. Pieces of monitoring substances (such as ferro-elastic or piezo-electric materials) are embedded in a physical medium which undergoes curing or setting process which may generate a pressure induced polarization or other changes in physical properties. The physical medium may include but not limited to: glue, epoxy, concrete, sealant, soil, asphalt, ink, gel or any other artificial and/or biological substance or compound which is changing during its manufacturing, transportation or storage. Graph 500 illustrates capacitance (by way of example) of a monitoring substance as a function of time during curing process (curing process for example is the process of glue or concrete when setting from liquid to solid). During the curing process, the physical medium introduces pressure changes to the monitoring substance (usually increase in pressure) until a steady state is achieved. When a monitoring substance such as a ferro-elastic monitoring element is added during the curing process of an article, the pressure may generate a pressure-induced polarization to the ferro-elastic monitoring substance, and a partial or full polarization may occur which may be monitored as capacitance over time (different characteristics of the polarization effect on the monitoring element may be monitored not just capacitance). Monitoring the pressure induced polarization on the monitoring substance may indicate manufacturing process parameters such as: authentication, strength, quality, substance mix ratio and more. Thus, any deviation from a predefined manufacturing process may be recorded and detected as a change to the one or more physical properties of the substance embedded within the physical medium. The monitored change may be evident of a non-authentic manufacture process or a non-compliant product in view of specified quality assurance requirements, and may further used for calibrating the reading of the acoustic sensors.

For example, such deviation from a specified manufacturing process may be seen in graph 500. An exemplary non-limiting manufacturing parameter (e.g., capacitance) is shown over time in plot line 501 representing substance having a mix ratio of 100:38, whereas a deviation of a predefined threshold from plot line 501 may be seen plot line 502 representing substance having a different mix ratio of 100-60.

When a monitoring substance such as pressure-induced Ferro-elastic monitoring element is introduced, different types of graph behavior may indicate different types of physical media or different type of manufacturing process, with the graphs indicating different points such as point 502 which exhibits the exothermic maximum, point 501 which may indicate substance gelation start and point 503 which may reflect the gelation end point. The ability to measure physical properties of the monitoring substance which indicate a physical change to the article of manufacture may be used to determine authenticity, quality, mix ratio strength and other parameters of the article of manufacture deriving from the manufacturing process or from different curing procedures (such as applying concrete in a building). This can be achieved by knowing the monitored article of manufacture, what kind of process it underwent during the manufacturing, and comparing it to data stored and applicable to the known process and its effects on the same article of manufacture. The comparison may indicate whether the process complied with the predefined process and article definitions. In cases of epoxy curing or concrete setting time, the required quality of the article final stage may be evaluated based on the final steady state indicated at its beginning in point 503 and thereafter. In different types of articles, mixing ratios points 501, 502, 503 and the overall graph behavior may change to indicate either a non-authenticated process or a low quality of article used compared to a good quality article graph. A threshold may be used in order to indicate the allowed deviations from a good quality reference. In case of detecting and monitoring different mix ratios in an article of manufacture when analyzing an article having mix ratio of 100-38 (solid line), an article having mix ratio of 100-60, an article having mix ratio of 100-24, and by knowing the behavior and characteristic of each mix ratio, monitoring the article of manufacture may be achieved by monitoring the capacitance of the monitoring substance graph and report if the mix ratio is not compatible with the required manufacturing process. In another case, when a settling time of epoxy or concrete (or other substance) is being measured, the graph behavior and point 501, 502, 503 may indicate the strength of the article and its overall quality. Parameters such as mix ratio, mix amount, gelation time and others may be controlled and predefined in order to create a unique ID of the process which may indicate the authenticity of the article and whether it had undergone the proper manufacturing process. Using the monitoring ferro-elastic embedded in the article (such as concrete in a building, or epoxy in a chip) may indicate during the life cycle of the article if any changes to the pressure induced polarization on the monitoring substance has occurred, and these changes may indicate that the article may experience different changes in strength, moisture, stability, vibrations and other characteristics of the article. The changes may be transmitted to a remote monitoring station, which may collect the data and report an alert to the end user. For example, if a monitoring ferro-elastic substance is embedded in different buildings, an earth quake may change the steady state of the pressure induced polarization of the monitoring element and thus may indicate according to reading from different places that an earth quake event has occurred.

According to some embodiments of the present invention, the ferro-elastic substance may undergo structural phase transition. The structural phase transition may include a pressure induced polarization of the ferro-elastic substance.

According to some embodiments of the present invention, the ferro-elastic substance post pressure induced polarization has unique properties that may be used for at least one of: authentication, manufacturing process monitoring, and usage monitoring of said article of manufacture.

According to some embodiments of the present invention, the piezo-electric substance comprises a ceramic substance.

According to some embodiments of the present invention, the at least one physical property comprises a polarity state of the piezo-electric substance.

According to some embodiments of the present invention, the polarity state of said piezo-electric substance may be poled in the first phase and un-poled in the second phase.

Figure 6A:
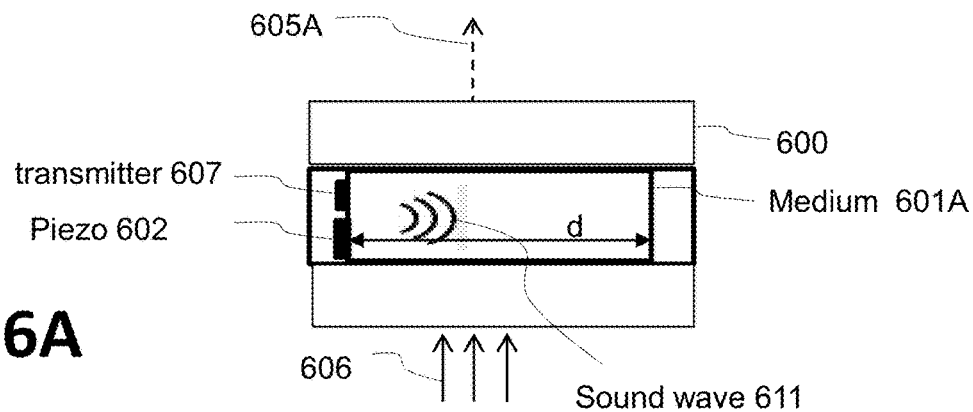
FIGS. 6A, 6B, and 6C show a diagram illustrating an acoustic pulse generator and a sensor device coupled to a physical medium being monitored on different times, in accordance with some embodiments of the present invention.
Figure 6B:
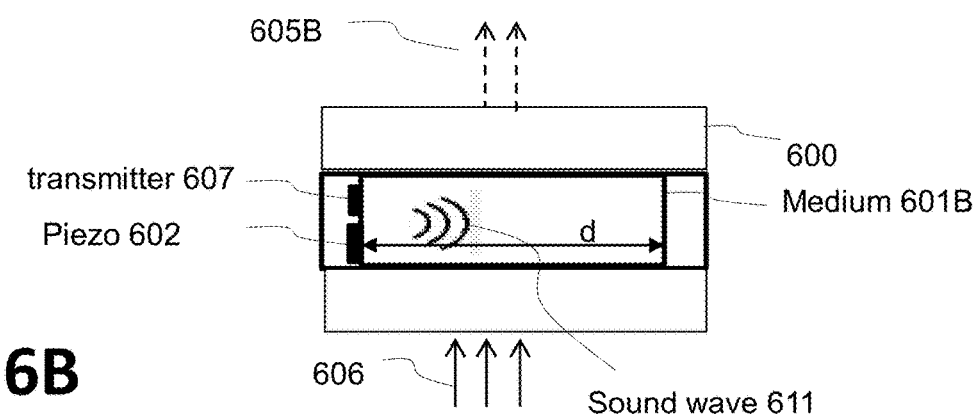
Figure 6C:
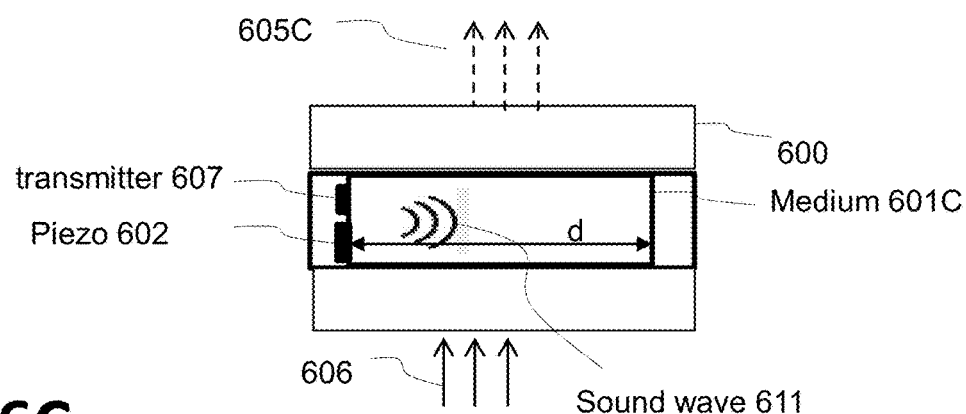

FIGS. 6A, 6B, and 6C illustrate a process of monitoring the physical condition of a medium (e.g., a filter) using a monitoring substance 602 embedded within medium 601A-C which may indicate the condition of the medium in combination with acoustic sensing. The condition of the medium may vary from a starting condition (newly prepared medium) 601A to midlife condition 601B and final condition 601C which indicates the medium is not safe anymore. the medium can be a filter that may be any component adapted to absorb some particles and, on the other hand, to allow other particles to pass (such as oil filter, gas filter, smoke and others). Monitoring substance 602 may be a piezo-electric monitoring element and is placed or embedded within physical medium 602, and transmitter 607 is placed within medium 602 either on the same side of the monitoring substance or on the other side of the medium. Transmitter 607 may generate a sound wave 611, which according to its velocity may generate a voltage fluctuation on the piezo-electric monitoring substance 602 which serves here as an acoustic wave sensor.

Formula (1) below illustrates the sound wave velocity relationship that corresponds with the operation of these sensors:

$$V_E = \sqrt{\frac{E}{\rho}} \qquad (1)$$

Wherein:
ρ density
K bulk modulus=1/compressibility
μ shear modulus
λ Lame's coefficient
E Young's modulus
ν Poisson's ratio
M P-wave modulus=K+(4/3)μ

Wherein d=distance between the filters wall, the distance the sound wave needs to travel and t=the time that took to the sound wave to reach the sensing element(piezo) using a standard timing device in equation (2) below:

$$V = \frac{d}{t} \qquad (2)$$

In a closed environment, the velocity of the sound wave would remain constant according to aforementioned equation (2), the distance d remains constant, and the sound wave parameters may be controlled, and thus the time to travel the same distance remains the same and so is the sound wave velocity. In case of a filter acting as a medium which conveys the sound wave a constant distance d, the filter may change its density and thus cause the sound wave to travel at different velocity, as indicated in aforementioned equation (1). Young's modulus E of the medium does not change, but the density of the medium may increase as the medium keeps absorbing particles during its working life cycle. Measuring the voltage received in the piezo-electric 602 monitoring substance indicates that a linkage between the velocity of a sound wave traveling between two side walls of the medium, using equation 1 where Young's modulus E is known and depends on the material, the velocity of the sound wave will change according to the density of the material inside the filter. The density of the material inside the filter is changing during the life cycle of the filter, as during the use of the filter some of the particles (such as oil) are absorbed in the filter and may change the filter density. The changes in the density will be translated to a reading in the piezo-electric sensor placed on the filter wall.

The initial process may start with a calibration step, which calibration step may take different reading of known physical media in different conditions, such as in the case of filters: a first filter in a new condition (not used), a second filter in midlife condition, and a third filter in its final condition (dead filter). Transmitting a sound wave 611 with known parameters and measuring the voltage fluctuation over time may indicate the stage of the filter within its life cycle (e.g., "new", "used" and "dead") and may be represented in look up table (LUT) as explained below.

FIG. 6A shows filter 601A in a first condition (new filter) situated or coupled to enclosure 600 which may allow fluid, gas or other working substances to flow through it. In FIG. 6A, working substance direction of flow is indicated by 606 as an inlet and by 605A as the outlet, and the number of arrows at 605A (three arrows in 606 and one arrow our at 606A) indicates that the filter is working properly and absorbing a good amount of the particles needed to be filtered. Transmitter 607 generates a sound wave with known properties which travels inside filter 601A in a certain velocity which is typical to a specific filter in a first condition (new filter). Piezo-electric monitoring substance generates voltage reading which may correspond to filter condition. Using a wireless transmitter (not shown) coupled to the monitoring substance may allow transmission of piezo-electric readings and of the corresponding filter condition to remote monitoring station or user.

FIGS. 6B and 6C are the same configuration showing the filter in different life conditions, as FIG. 6B indicates a midlife filter condition, whereas FIG. 6C shows a filter in the end life where outlet 605C shows that almost no absorption is done in the filter. In this case, the piezo-electric monitoring element will reach a steady state reading such as indicated in FIG. 3, point number 4. By transmitting the filter status to a remote location/user, a new filter may replace the old filter.

Figures 7A, 7B:
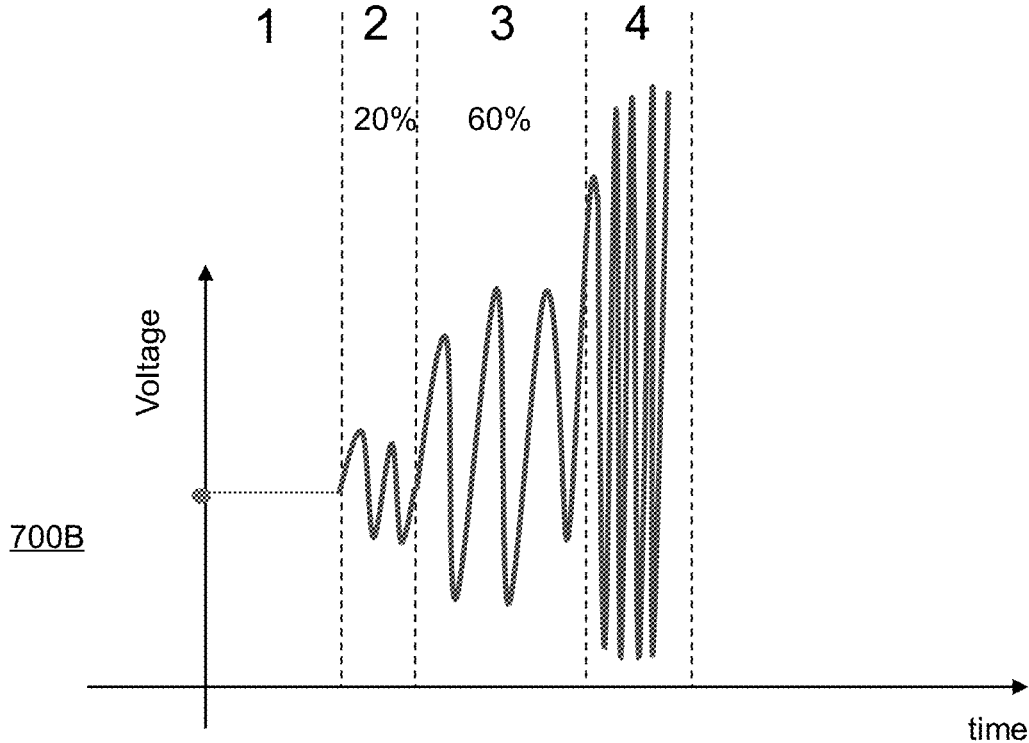
FIG. 7A shows table diagram illustrating non-limiting example of the monitored medium properties according to some embodiments of the present invention.
FIG. 7B shows graph diagram illustrating non-limiting example of the monitored medium properties according to some embodiments of the present invention.

FIG. 7A shows a table diagram illustrating a non-limiting example of the monitored medium properties, according to some embodiments of the present invention. The data is given in a form of a look up table (LUT) prepared in calibration phase, wherein the calibration or learning phase is done a priori to learn the filter (or the article of manufacture) behavior under different usage condition and life cycle.

FIG. 7B shows a graph diagram illustrating a non-limiting example of the monitored medium properties, according to some embodiments of the present invention. These are empirical data from which a LUT as illustrated above, may be created.

Figure 8:
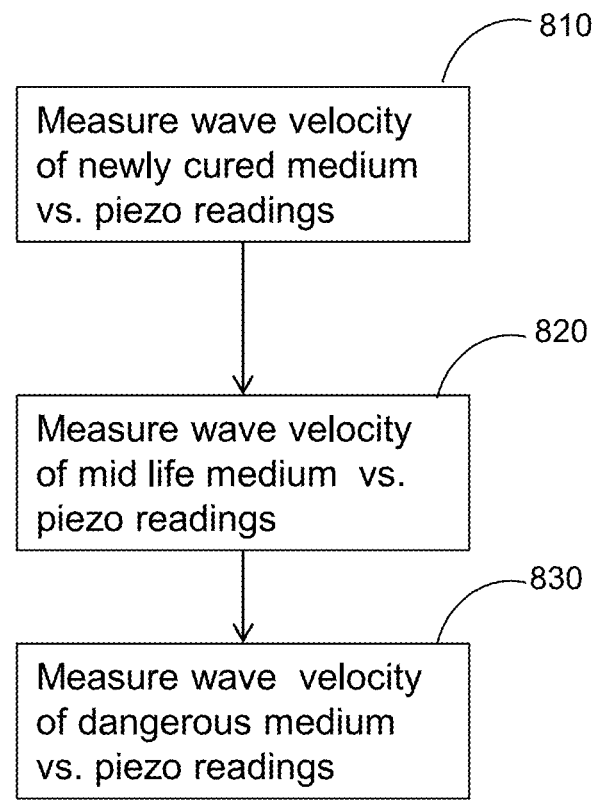
FIG. 8 shows a flowchart diagram of a method monitoring physical condition of a physical medium with embedded acoustic sensors calibrated by piezo-electric sensors, according to some embodiments of the present invention.

FIG. 8 shows a flowchart diagram of a method monitoring physical condition of a physical medium with embedded acoustic sensors calibrated by piezo-electric sensors, according to some embodiments of the present invention. Method 800 may include the following steps: coupling at least one substance portion comprising ferro elastic material to a compound, said substance portion being configured to change a polarization level thereof continuously in response to a strain gradient applied thereto over said a transient period which results in said modification 810; sensing a physical property of said substance portion affected by the polarization level of said substance portion, due to said modification 820; and determining, using a computer processor, said modification, based on the sensed physical property of said substance portion 830.

According to some embodiments of the present invention, the transient period may be a time in which said compound changes from one state to another state or may be a time in which said compound undergoes solidifying. The transient period is simply the time over which there is a noticeable and detectable change in the compound.

According to some embodiments, the modification may be a different metric per the compound under test. In a case that the compound is concrete, the modification metric may be compression strength (e.g., standard ASTM C39). For glues, the respective modification metric would be glass transition temperature.

The aforementioned flowchart and block diagrams illustrate the architecture, functionality, and operation of possible implementations of systems and methods according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Figure 9:
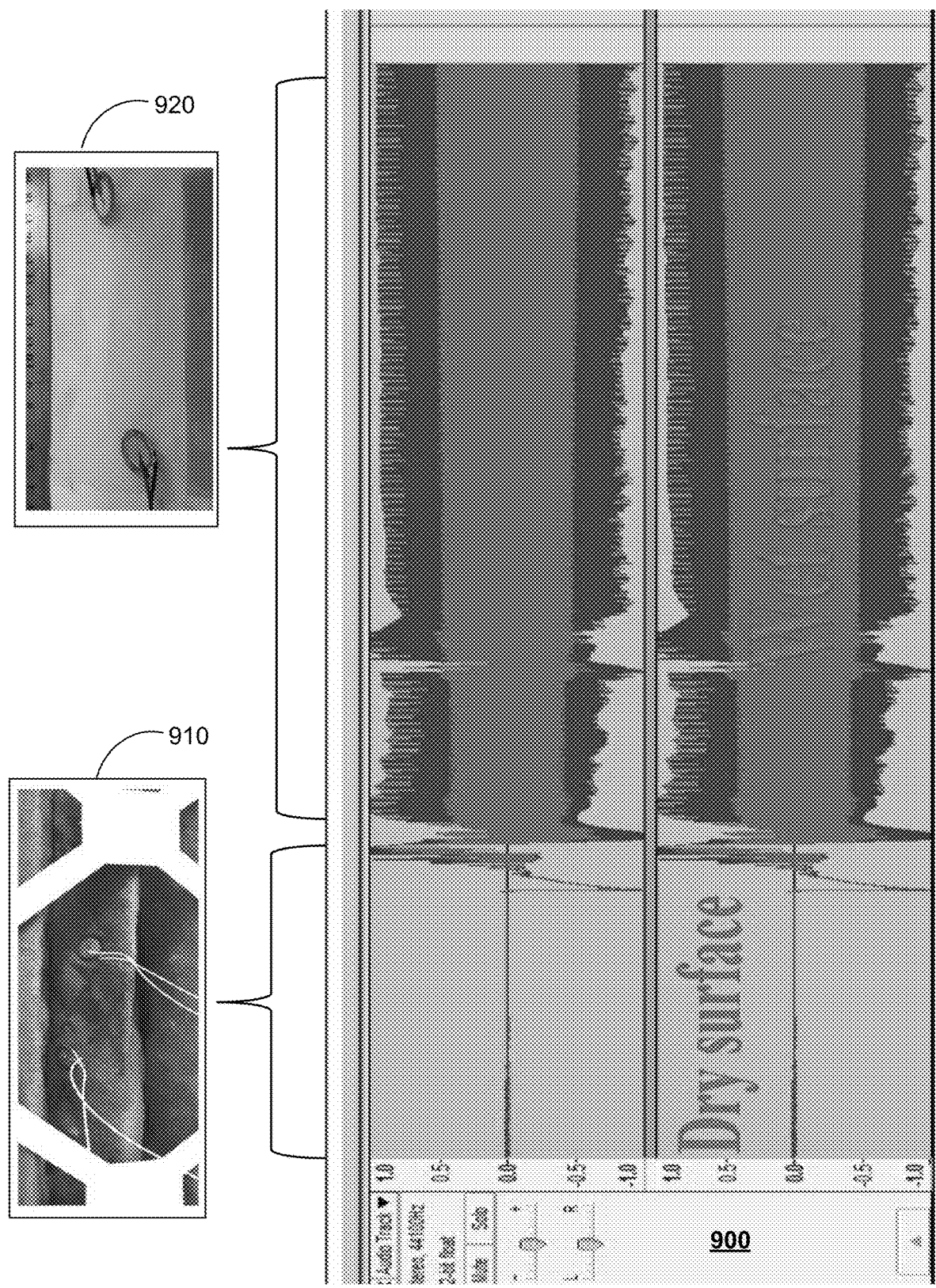
FIG. 9 is a graph diagram showing experimental results illustrating non-limiting example of the monitoring physical properties of a physical medium using acoustic sensors embedded therein, according to some embodiments of the present invention.

FIG. 9 illustrates non-limiting examples of the monitoring substance properties, according to some embodiments of the present invention. Picture 910 depicts a filter in a first condition (new) including a transmitter and receiver. Picture 920 is in the same configuration, depicting the filter in a different condition, later in its life (used), again including a transmitter and receiver. Graph 900 depicts the change in signal between the two transmitters (new and used), wherein the new transmitter is in a dry condition and the used transmitter is in a wet condition.

Figure 10:
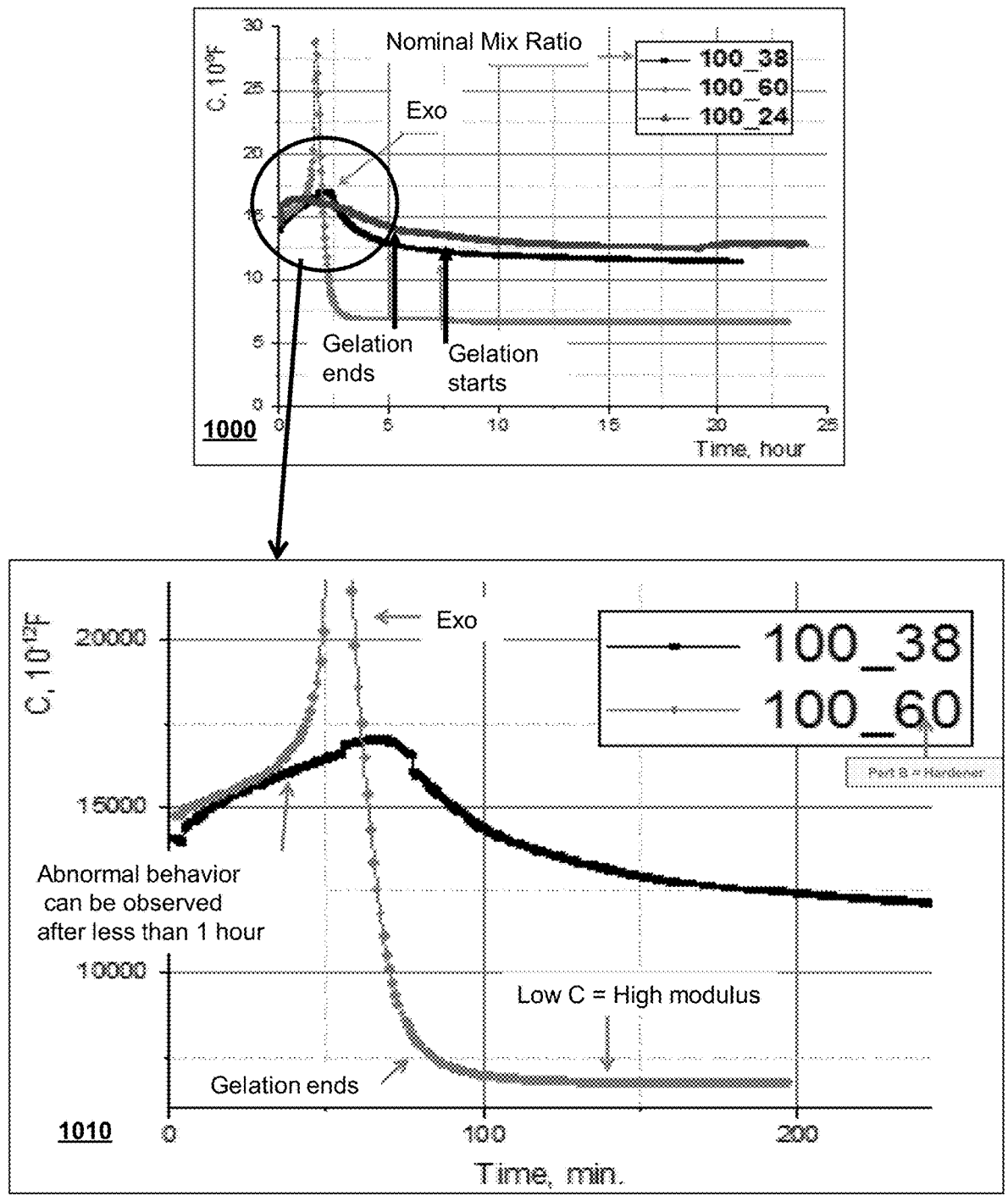
FIG. 10 is a graph diagram showing experiment results illustrating non-limiting example of the observed change in some physical properties in a physical medium according to some embodiments of the present invention.

FIG. 10 illustrates a graph in which the changing behavior of substances with different nominal mix ratios can be observed. The start and end of gelation periods are clearly marked, alongside periods of abnormal behavior and regions at which the substances may harden.

In the reminder of the description, the term "detector" or "detectors" may relate to the aforementioned ferro-elastic substance portions configured to undergo a pressure-induced polarization, that may be later sensed and used to monitor the modification to the compound to which they are coupled.

Figure 11:
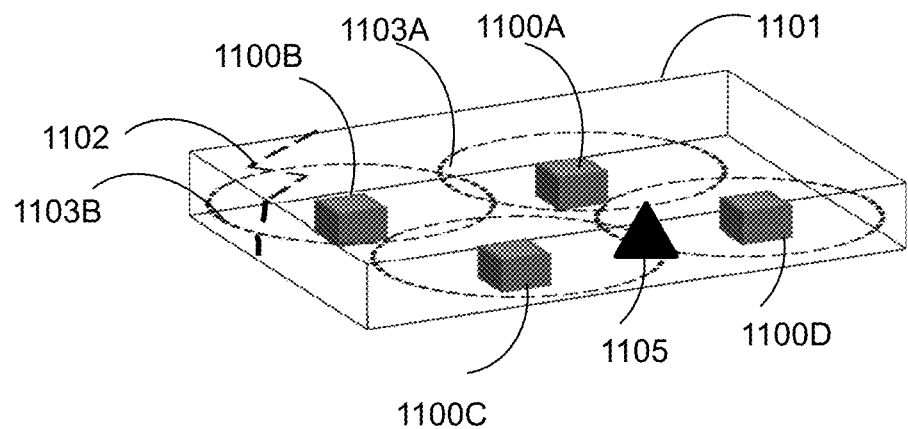
FIG. 11 is a block diagram illustrating a possible arrangement of the sensors within the physical medium in accordance with some embodiments of the present invention.

FIG. 11 is a diagram illustrating a possible arrangement in accordance with some embodiments of the present invention. In this arrangement, an array of detectors 1100A-1100D made of the ferro-elastic substance portions are coupled or embedded within compound 1101 and each can be sensed as explained above to determine modification and strain within compound 1101 in the transient period and also in the steady state period after the transient period ended. Thus, a crack such as 1102 occurring during transient period or the steady state may affect the pressure or strain and based on the difference in level of strain measured by the detectors and may be detected. Similarly, using triangulation based on the respective radii surrounding the detectors (such as 1103B or 1103A), an event 1105 that affects strain gradient may be detected and located. The event may occur either during the transient period or in the steady state.

Figure 12:
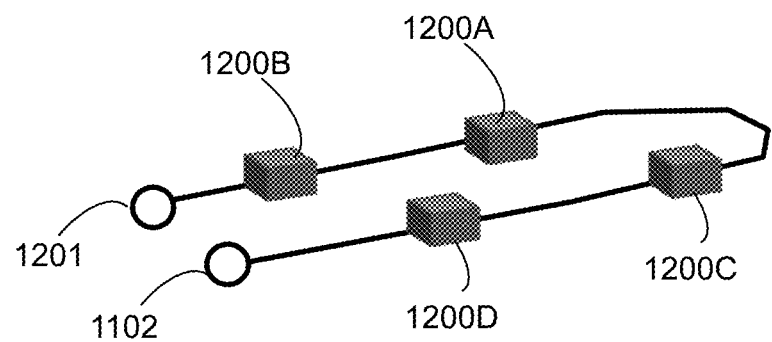
FIG. 12 is a block diagram illustrating another possible arrangement of the sensors within the physical medium in accordance with some embodiments of the present invention.

FIG. 12 is a diagram illustrating a possible arrangement in accordance with some embodiments of the present invention. In this arrangement, several detectors 1200A-1200D are connected in series and over a cable with two nodes 1201 and 1202 that can be connected to a network. The connection in series is advantageous in using minimal wiring and easy deployment. It is also advantageous as all detectors share the same communication and power wiring. Point 1802 can be located in a secure position not affected by the concrete and can be thus easily connected to other networks without interference. Additionally, it can be used for getting a good averaging of the strain gradient within the compound under test.

Figure 13:
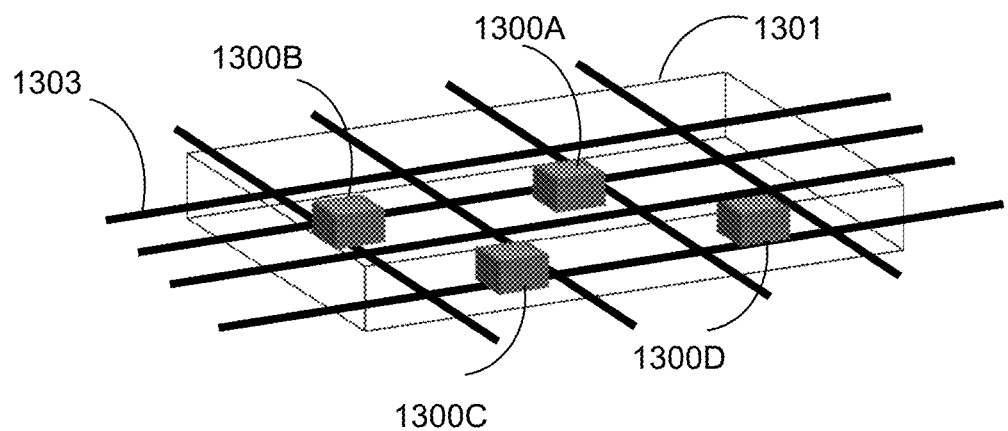
FIG. 13 is a block diagram illustrating yet another possible arrangement of the sensors within the physical medium in accordance with some embodiments of the present invention.

FIG. 13 is a diagram illustrating a possible arrangement in accordance with some embodiments of the present invention. In this arrangement, possibly an already existing grid of metal 1303 (used for structural reasons) embedded within the compound under test 1301 (e.g., concrete) serves as a wiring network of the array of detectors of ferro-elastic substance 1300A-1300D. This arrangement of parallel wiring is advantageous in allowing a better localization of strain-related events occurring during steady state phase, is since each detector can be monitored individually. Additionally, the metal grid may serve as infrastructure for delivering power and communication for the array of detectors.

Figure 14:
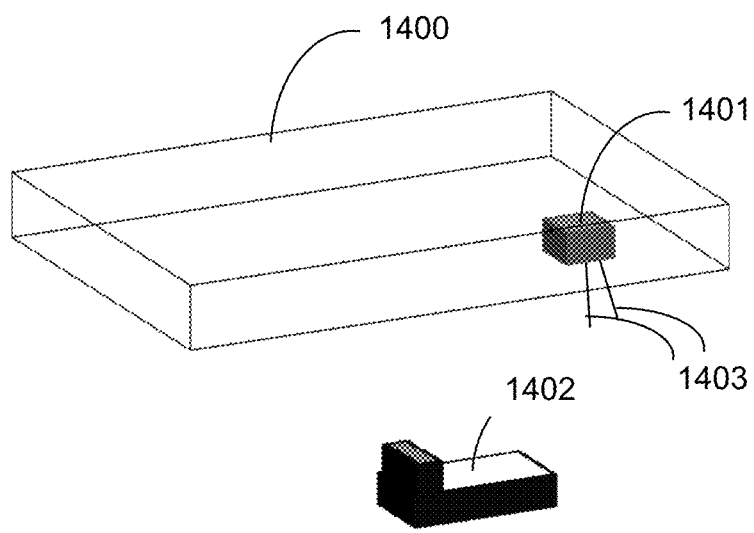
FIG. 14 is a block diagram illustrating yet another possible arrangement of the sensors within the physical medium in accordance with some embodiments of the present invention.

FIG. 14 is a diagram illustrating a possible arrangement in accordance with some embodiments of the present invention. In this arrangement, a smartphone 1402 or any device with wireless connectivity (e.g., dedicated sensing device, possibly installed on drones) may be used to sense levels of strain gradient within compound 1400 as applied to ferro-elastic detector 1401 which is provided with wireless connectivity. Alternatively, monitoring is carried out via pins 1403. Alternatively, the communication with detector 1401 may be carried out via near field communication (NFC).

Figure 15:
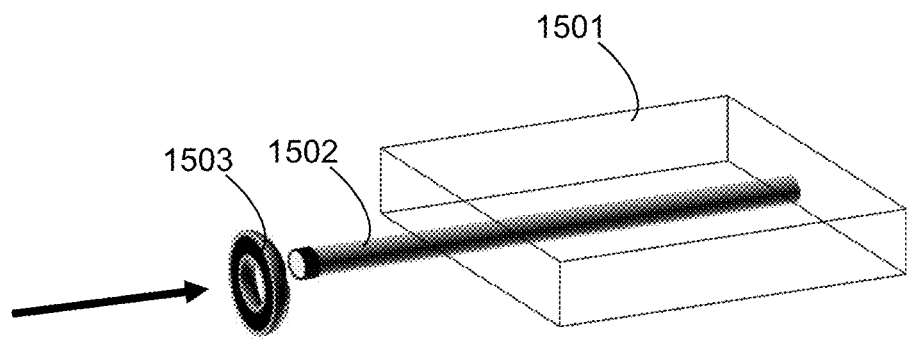
FIG. 15 is a block diagram illustrating another possible structural arrangement of the sensors within the physical medium in accordance with some embodiments of the present invention.

FIG. 15 is a diagram illustrating a possible arrangement in accordance with some embodiments of the present invention. In this arrangement, it is shown how a detector embedded within a ring (such as a rubber ring 1503) may be easily attached to a structural metal rod 1502 used for structural reasons in a concrete block 1601. This embodiment is a retrofit arrangement that is using existing infrastructure (metal grid) for stabilizing and possibly wiring the detector to a network.

Figure 16:
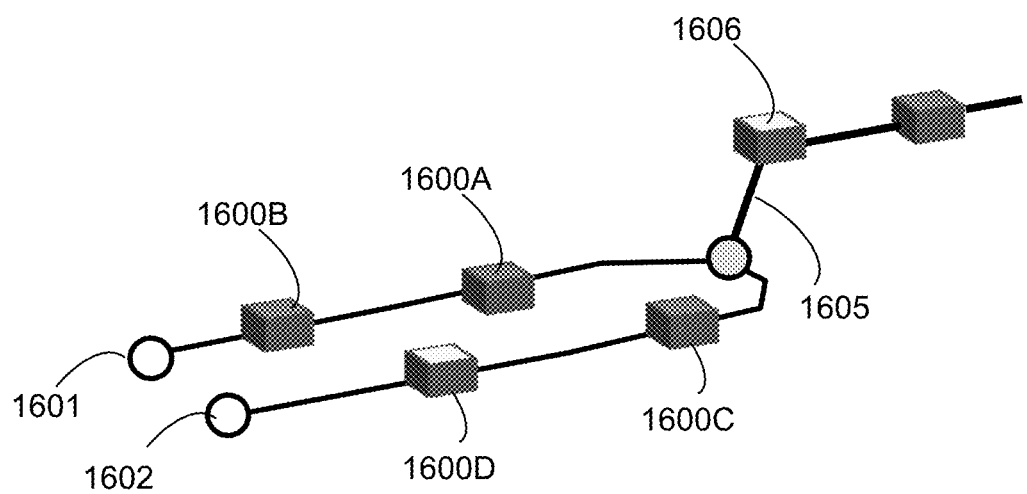
FIG. 16 is a block diagram illustrating another possible logical/electrical arrangement of the sensors within the physical medium in accordance with some embodiments of the present invention.

FIG. 16 is a diagram illustrating a possible arrangement in accordance with some embodiments of the present invention. This arrangement shows how several detectors 1600A-1600D can be deployed in an ad hoc network in which super node 1600D can collect readings from ordinary nodes 1600A, 1600B and 1600C and convey it to another network 1605 and possibly super node 1606 and from there to further networks via further super nodes. Advantageously, this arrangement contributes to scalability of the present invention.

In the above description, an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions. It will further be recognized that the aspects of the invention described hereinabove may be combined or otherwise coexist in embodiments of the invention.

It is to be understood that the phraseology and terminology employed herein is not to be construed as limiting and are for descriptive purpose only. The principles and uses of the teachings of the present invention may be better understood with reference to the accompanying description, figures and examples. It is to be understood that the details set forth herein do not construe a limitation to an application of the invention.

Furthermore, it is to be understood that the invention can be carried out or practiced in various ways and that the invention can be implemented in embodiments other than the ones outlined in the description above. It is to be understood that the terms "including", "comprising", "consisting" and grammatical variants thereof do not preclude the addition of one or more components, features, steps, or integers or groups thereof and that the terms are to be construed as specifying components, features, steps or integers.

While the invention has been described with respect to a limited number of embodiments, these should not be construed as limitations on the scope of the invention, but rather as exemplifications of some of the preferred embodiments. Other possible variations, modifications, and applications are also within the scope of the invention.

The invention claimed is:

1. A method of monitoring a change in physical properties of a media over time, the method comprising:
    embedding a plurality of acoustic sensors into a physical medium before curing thereof; transmitting an acoustic wave by at least one transmitter coupled to or embedded within said physical medium;
    repeatedly calculating, over different points of time, a travel time of said acoustic wave between the at least one transmitter and the plurality of acoustic sensors; and
    analyzing said travel times, to detect a change over time in physical properties of said physical medium associated with said travel time,
    wherein the physical medium exhibits an acoustic coefficient which is uniform throughout.

2. The method according to claim 1, wherein the acoustic waves are coded by assigning a unique signal coding linked to a direction of each one of the acoustic waves so that each of the calculated travel time is associated with a different location of the sensors.

3. The method according to claim 1, further comprising using the acoustic sensors to monitor curing parameters characterizing a transient period of the physical medium, wherein the analyzing of said travel times, to detect a change over time in physical properties of said physical medium, is further based on said curing parameters.

4. The method according to claim 3, wherein said acoustic sensors comprise piezo electric sensors that are sensitive to said acoustic waves and further sensitive to strain gradient in said physical medium during said transient period.

5. The method according to claim 3, further comprising:
    embedding ferro elastic sensors in said physical medium before or during the curing process; and
    using reading from the ferro elastic sensors to obtain curing parameters of the physical medium.

6. The method according to claim 5, wherein the using of the ferro-elastic sensors to obtain curing parameters of the physical medium is carried out in an early stage of said transient period, and wherein the using of the acoustic sensors to obtain curing parameters of the physical medium is carried out in a late stage of said transient period.

7. The method according to claim 1, wherein the analyzing is further carried out by comparing values of the travel times to a historical database associated with changes over time of said physical properties of said media.

8. The method according to claim 1, wherein said acoustic wave is an ultrasonic wave having a frequency range of 20 kHz to 100 kHz.

9. A system of monitoring a change in physical properties of a media over time, the system comprising:
    a plurality of acoustic sensors embedded within a physical medium before curing thereof;
    a transmitter coupled to or embedded within said physical medium which transmits one or more acoustic waves; and
    at least one computer processor which repeatedly calculates, over different points of time, a travel time of said acoustic wave between the at least one transmitter and the plurality of acoustic sensors,
    wherein said computer processor analyzes said travel times, to detect a change over time in physical properties of said physical medium associated with said travel time,
    wherein the physical medium exhibits an acoustic coefficient which is uniform throughout.

10. The system according to claim 9, wherein the acoustic waves are coded by assigning a unique signal coding linked to a direction of each one of the acoustic waves so that each of the calculated travel time is associated with a different location of the sensors.

11. The system according to claim 9, wherein the computer processor uses the acoustic sensors to monitor curing parameters characterizing a transient period of the physical medium, wherein the analyzing of said travel times, to detect a change over time in physical properties of said physical medium, is further based on said curing parameters.

12. The system according to claim 11, wherein said acoustic sensors comprise piezo electric sensors that are sensitive to said acoustic waves and further sensitive to strain gradient in said physical medium during said transient period.

13. The system according to claim 11, further comprising: ferro elastic sensors embedded in said physical medium before the curing process, wherein the computer processor uses reading from the ferro-elastic sensors to obtain curing parameters of the physical medium.

14. The system according to claim 13, wherein the using of the ferro-elastic sensors to obtain curing parameters of the physical medium is carried out in an early stage of said transient period, and wherein the using of the acoustic sensors to obtain curing parameters of the physical medium is carried out in a late stage of said transient period.

15. The system according to claim 9, wherein the analyzing is further carried out by comparing values of the travel times to a historical database associated with changes over time of said physical properties of said media.

16. The system according to claim 9, wherein said acoustic sensors are retrofitted and wired into a metal grid within the physical medium.

17. The system according to claim 13, wherein said ferro elastic sensors are retrofitted and wired into a metal grid within the physical medium.

18. The system according to claim 9, wherein the transmitter is connected to a smartphone, and wherein the at least computer processor is located on a server and on said smartphone.

* * * * *